United States Patent [19]
Dirico et al.

[11] Patent Number: 4,825,804
[45] Date of Patent: May 2, 1989

[54] VERTICALLY RETRACTING COATER

[75] Inventors: Mark A. Dirico, Quincy, Mass.; Phillip Rodriguez, Garland, Tex.

[73] Assignee: Dahlgren International, Inc., Dallas, Tex.

[21] Appl. No.: 42,374

[22] Filed: Apr. 24, 1987

[51] Int. Cl.⁴ .......................................... B05C 11/00
[52] U.S. Cl. ...................................... 118/46; 118/262
[58] Field of Search .................................. 118/46, 262

[56] References Cited

U.S. PATENT DOCUMENTS

| | | | |
|---|---|---|---|
| 3,433,155 | 3/1969 | Norton | 118/262 X |
| 3,768,438 | 10/1973 | Kumpf | 118/626 |
| 4,147,126 | 4/1979 | Riggs | 118/227 |
| 4,270,483 | 6/1981 | Butler | 118/46 |
| 4,329,387 | 5/1982 | Goodrich | 428/196 |
| 4,685,414 | 8/1987 | Direco | 118/46 |

FOREIGN PATENT DOCUMENTS 1123267 5/1982 Canada.
2068298 8/1981 United Kingdom.

OTHER PUBLICATIONS

Booth, Coating Equipment and Process N.Y., Lockwood Publishing Co., Inc., pp. 149-153, 1970.

Primary Examiner—Shrive Beck
Assistant Examiner—Alain Bashore

[57] ABSTRACT

A retractable coater is used on-line with the last unit of a standard offset lithographic printing press. The coater includes a coating assembly mounted on a platform and a retraction guide assembly, the latter comprising:
(i) a horizontal member and means for slidably supporting platform movement along the horizontal member;
(ii) a vertical member slidably guiding vertical movement of the platform and
(iii) means for slidably lifting the platform and coating metering assembly on a course guided by the vertical member.

14 Claims, 4 Drawing Sheets

VERTICALLY RETRACTING COATER

BACKGROUND OF THE INVENTION

This invention relates to apparatus for coating a moving web, which is used on-line with a standard off set lithographic printing press unit.

As described in commonly owned, allowed U.S. patent application Ser. No. 719,474, now U.S. Pat. No. 4,685,414, which is hereby incorporated by reference, the final unit of a multi-unit lithographic press can be used to apply coatings. Specifically, a textured roller and coating feed mechanism are fixed to a movable platform, which is locked in place to meter coating to the blanket cylinder of the final press unit. The blanket transfers coating to the workpiece.

As further disclosed in Ser. No. 719,474, when the final unit is needed to print an additional color, the platform, together with the textured roller and the coating feed (including a doctor blade assembly), can be disengaged and moved horizontally away from the final press unit. The dampener and inking mechanisms of the final press unit are then used for off set lithographic printing in the conventional manner.

SUMMARY OF THE INVENTION

The invention generally features a retractable coater for use on-line with the last unit of an off set lithographic printing press. The coater includes a coating assembly mounted on a platform and a retraction guide assembly, the latter comprising:

(i) a horizontal member and means for slidably supporting platform movement along the horizontal member;

(ii) a vertical member slidably guiding vertical movement of the platform and (iii) means for slidably lifting the platform and coating metering assembly on a course guided by the vertical member.

Preferred embodiments of the invention include the features described below. The horizontal member is a shaft, or like guide member, attached along the outside of the press unit and the platform is adapted to engage a support cooperatively and slidably engaging the shaft. A vertical shaft extends from the platform support (to which the vertical shaft is attached), through an opening in the platform, to a guide block positioned above, and attached to, the support, so that the platform slidably engages the vertical shaft to guide vertical movement of the platform. A lift arm is connected to the platform and to a drive means, e.g. to a force-receiving member that is driven by a force delivering means. Lift is achieved using a pair of hydraulic cylinders, positioned on opposite sides of the platform and connected to hydraulic pressure means through a pressure-compensated flow divider that is adapted to maintain equal flow to each cylinder. In that way, the platform is kept level.

The above-described apparatus improves the ability to use the final press unit for two functions: coating and printing. Specifically, the invention enables the press operator to reliably engage the coating assembly to, and disengage the assembly from, the blanket roll of the final unit, for use as a coater. The invention further enables the operator to disengage the coating assembly and move it away from the final press unit both horizontally and vertically, so that the unit may be used as a conventional lithographic press unit. The vertical lift feature is particularly advantageous because it gives the press operator substantial access to the area between the press delivery, i.e. that region of the press which receives the finished work-product and stacks it for further processing, and the last printing unit. The coating assembly is self-contained and can easily be moved into and out of the operable position with very simple manipulations, yet the assembly is reliably guided and locked for use in a demanding environment.

Other features and advantages of the invention will be apparent from the following description of a preferred embodiment thereof.

DESCRIPTION OF THE PREFERRED EMBODIMENT DRAWINGS

STRUCTURE

In FIGS. 1-4, the detachable coater assembly 10 generally includes the features described in greater detail in U.S. Ser. No. 719,474, referenced above, and there is no need to repeat that description here. The major components of coater assembly 10 are a textured applicator roller 12, a metering doctor blade (not shown), and a coating supply (not shown). The doctor blade and coating supply form a single assembly. Those basic features function generally as described in the '474 application.

Figure 1:
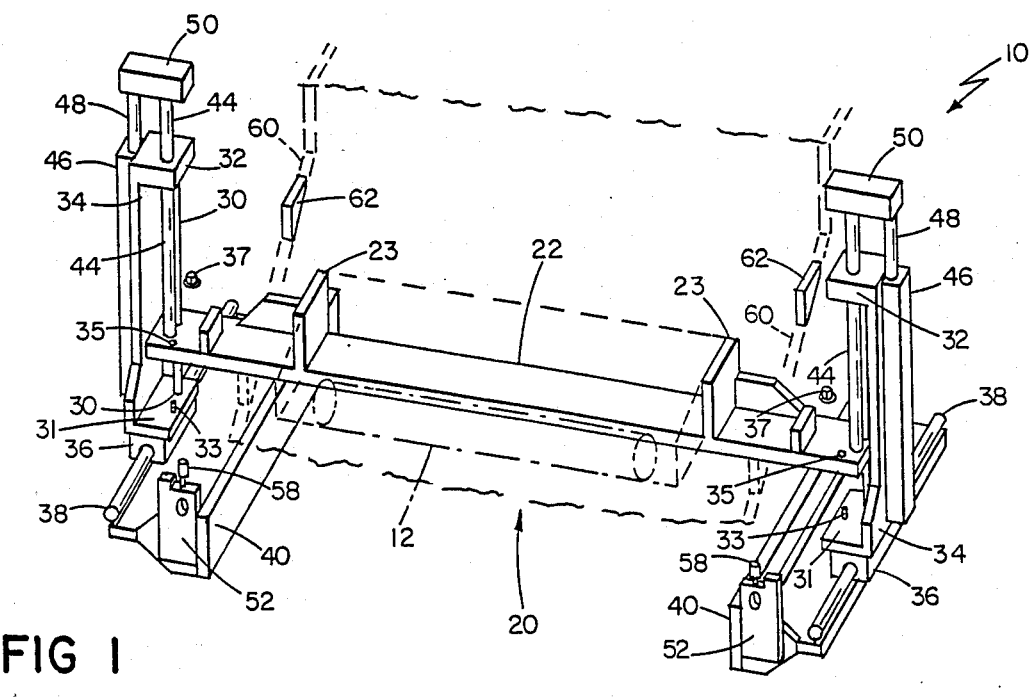
FIG. 1 is a perspective view of a detachable coater, without the adjacent standard lithographic press unit, with parts omitted and parts shown in broken line for clarity.

This invention generally features the carriage and retraction mechanism for the above-described coater. In FIG. 1, the carriage platform 20 features a base support frame 22 spanning horizontally across press unit. Side frames 23 and 24 extend vertically upward on opposite sides of support frame 22, to support the mounts for the coater assembly. Accordingly, the entire coater assembly is rigidly supported by base frame 22, and retraction movement of frame 22 retracts the coater assembly.

The retraction and lift features on one end of frame 22 are described, with the understanding that the features on the opposite side are identical. Frame 22 is rigidly attached at each end to a vertical lift shaft 44. Shaft 44 extends through an upper bearing block assembly 32. Bearing block assembly 32 is supported by by a vertical support bar 34, connected to a pillow block bearing 36. Pillow block bearing 36 slidably surrounds slide shaft 38 which is supported by bracket 40, which in turn is bolted to the press frame wall 60. It is important to note that bracket 40 extends along the outside of frame wall 60 to support slide shaft 38 in the direction of the press delivery area 130.

Also extending upwardly from block bearing 36 is guide shaft 30, which slidably extends through frame 22 to upper bearing block assembly 32. Hydraulic cylinder 46 is attached to the side of support bar 34 and controls a lift rod 48 which extends to force plate 50 upward, and thereby to lift shaft 44 and frame 22.

Figure 2:
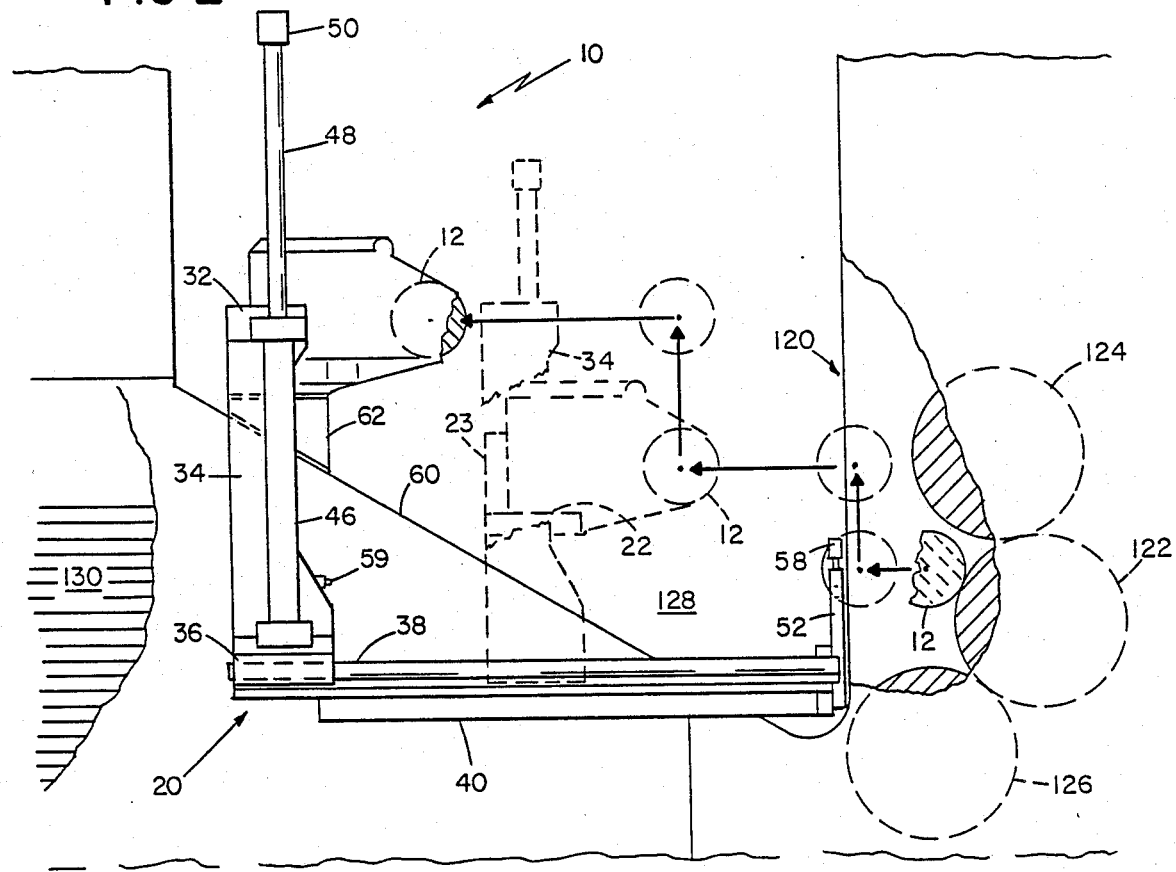
FIG. 2 is a side view of the detachable coater of FIG. 1, with an alternate position shown in broken lines, with parts broken away and in section.
Figure 3:
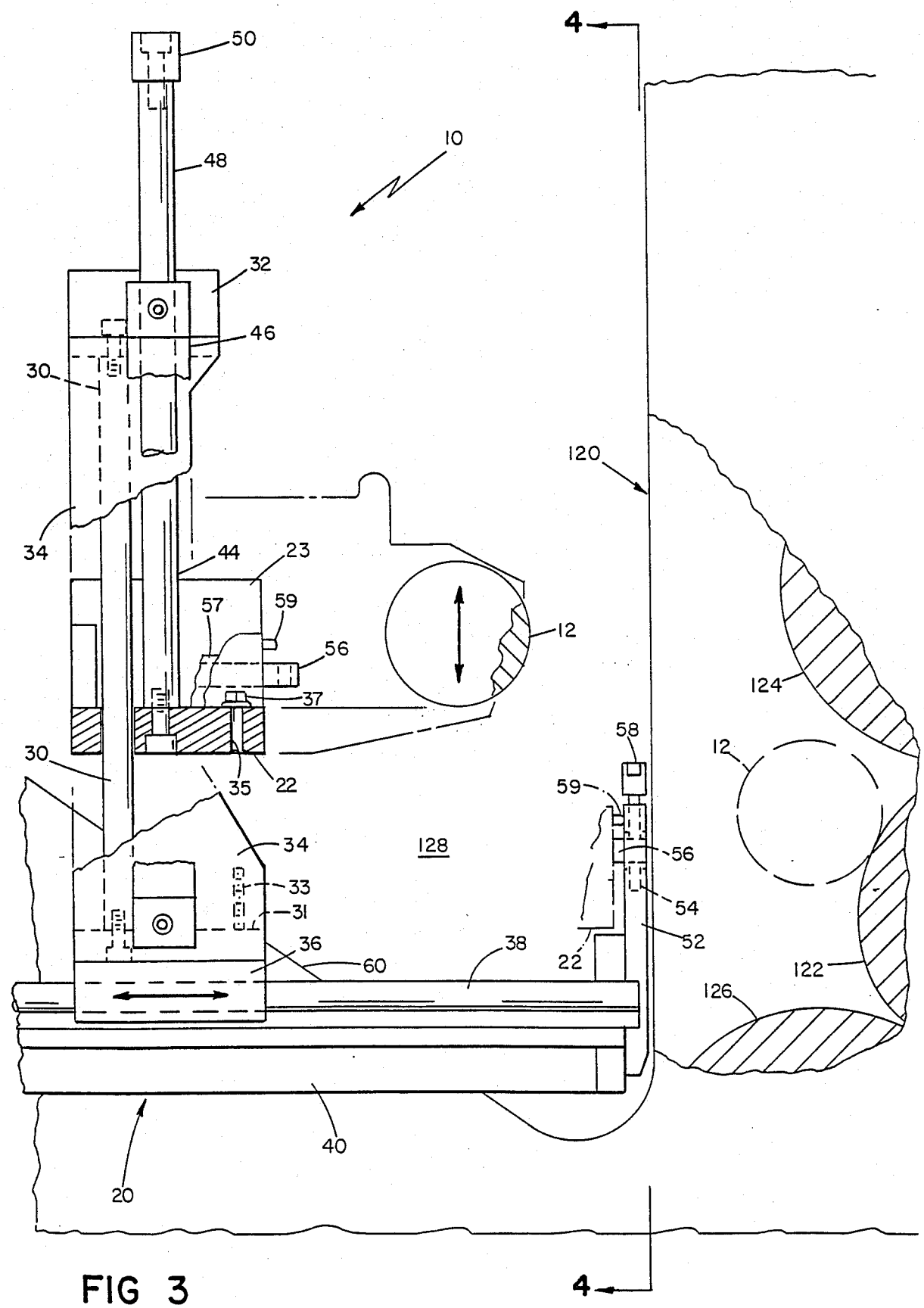
FIG. 3 is a side view of the detachable coater of FIG. 1, showing the laching mechanism, with parts broken away and in section.
Figure 4:
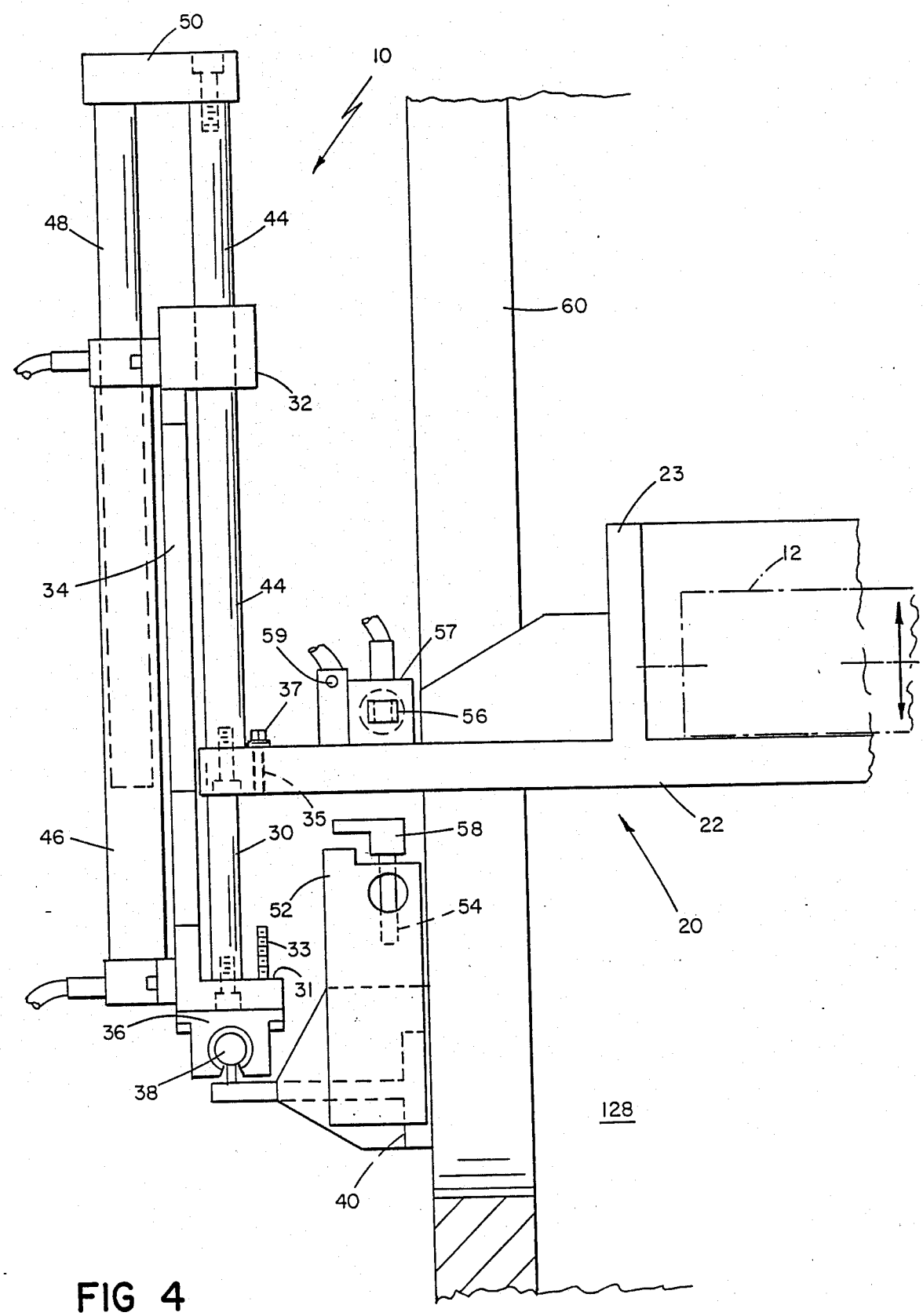
FIG. 4 is a front view of one side of the detachable coater, taken along 4—4 of FIG. 3.

As best shown in FIGS. 2-4, press unit 120 includes a blanket cylinder 122, a plate cylinder 124, and an impression cylinder 126. The workpiece is transfered by additional cylinders (not shown) under well 128 to a workpiece delivery area 130, where the work can be delivered and periodically transferred elsewhere.

Each of the two plates 52 on the front of well 128 of press unit 120 has a vertical slot sized and shaped to receive a lock pin 54 (FIG. 3). A horizontal opening to the slot receives the cylinder shaft 56 (FIG. 4) of hydraulic cylinder 57. Pin 54 cooperatively engages a slot in shaft 56 when handle 58 is engaged, to a locking position. Removal of handle 58 and pin 54 releases shaft 56. The locking mechanism allows the coating assembly to be locked into place, with a repeatable, desired resilient tension. An adjustable stop 59 is positioned adjacent cylinder 57. Plate 52 may be mounted to 40 as shown or directly to wall 60 as disclosed in patent '474.

The wall 60 of press unit 120 slants diagonally downward from its highest point at press delivery 130. A support bracket 62 is bolted to wall 60 in position to support the ends of frame 22 when the coating assembly is fully raised and retracted.

Figure 5:
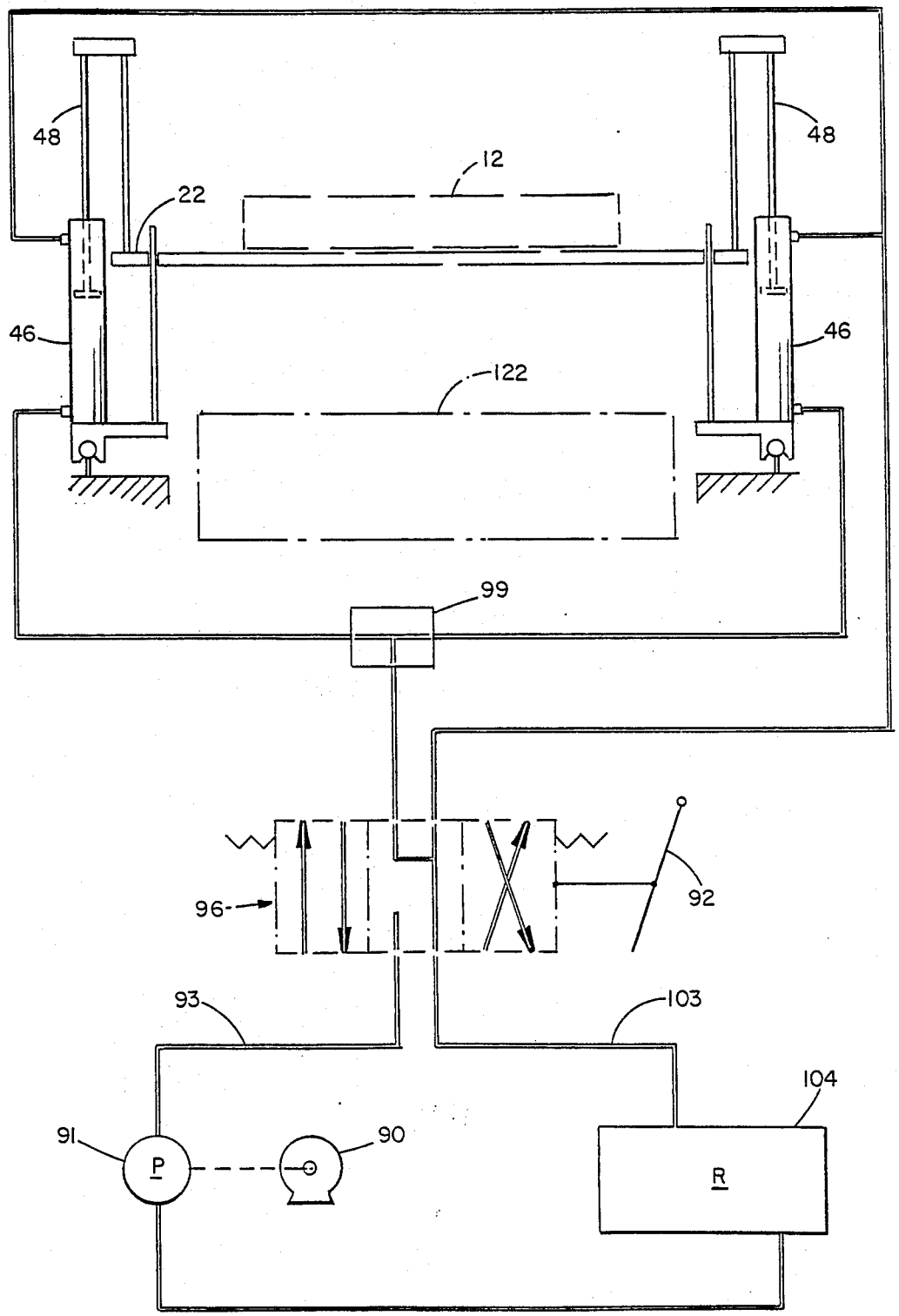
FIG. 5 is a diagram of the hydraulic circuitry of the detachable coater of FIG. 1.

FIG. 5 shows the hydraulic power system for the retractor. Electric motor 90 drives pump 91 to drive hydraulic fluid through supply line 93. Supply line 93 supplies directional valve 96, which, under the control of lever 92, determines which half of the hydraulic cylinders 46 receive flow from line 93. Downstream from directional valve 96, flow proceeds through a pilot check valve and a flow-control valve (not shown). Pressure-compensated flow divider 99 ensures that the flow is equal to each of the hydraulic retraction cylinders 46, so that the coater is automatically leveled. The return hydraulic flow is through a flow control valve and pilot check valve (not shown), directional valve 96, return line 103, reservoir 104 and, from there, to pump 91.

Operation

Initially, the coater assembly is in its retracted position, supported by brackets 62. In this position, the assembly is substantially out of the pressman's way, and the press unit is fully useful as an offset lithographic press unit. Specifically, the press unit and press delivery can be fully accessed and used substantially without interference from the coater. The pressman also has substantial access to blanket cylinder 122, as well to the ink and dampener rollers. The pressman also has access to the area underneath well 128, housing transfer rollers.

To convert the press unit to a coater, the coating assembly is guided horizontally along shaft 38 toward the blanket roll to free it from brackets 62. Pressure in hydraulic cylinders 46 is regulated so that lift rods 48 retract into the cylinders, allowing plate 22 to drop; in this way, the coating assembly is aligned (in one or more "steps" as shown in FIG. 2) vertically with the final press unit.

Specifically, vertical alignment is achieved when frame 22 seats on the lower horizontal surface 31 of support bar 34. To provide additional stabilization, threaded studs 33 on either side of surface 31 fit in corresponding openings 35 on frame 22, and flange nuts 37 are threaded on stud 33 to lock frame 22 to bar 34 and thereby stabilize the coater.

Once vertical alignment is achieved, the coating assembly is again advanced horizontally until hydraulic cylinder shaft 56 engages the opening in plate 52. Handle 58 and pin 54 are inserted to lock shaft 56 in place. Resiliently biased cylinder 57 absorbs any excess momentum from the moving coating assembly to prevent damage to the press unit. It also enables a pre-set pressure.

To convert the final unit to a standard printing unit, handles 58 and pin 54 are removed, flange nuts 37 are removed, and the carriage is moved horizontally and vertically to support bracket 62.

OTHER EMBODIMENTS

Other configurations and adaptations of the invention fall within the claims. For example, the lifting hydraulic cylinder can be oriented in the opposite direction, so that lift is achieved when the cylinder arm extends downwardly to press against a fixed support. In this case the body of the cylinder would more vertically with the coater unit while the extended shaft or piston would remain with the support. Multiple guide rods can be used to stabilize movement of the base frame.

We claim:

1. Apparatus for applying a liquid coating to the surface of a sheet work piece, said apparatus being adapted for operation on-line with the last unit of an off set lithographic sheet printing press, said press unit comprising a blanket cylinder and a work-piece delivery area, positioned on the opposite end of a well from said blanket cylinder, said apparatus comprising:

(a) a coating metering assembly supported by a platform comprising,
  (i) a rotably mounted applicator roller,
  (ii) coating delivery means positioned to deliver coating to said applicator roller, and
  (iii) a metering member mounted in position to control the amount of coating on said applicator roller; and
(b) a guide assembly adapted to retract said platform and said coating metering assembly away from said lithographic press unit, said guide assembly comprising
  (i) a horizontal member and means for slidably supporting said platform movement along said horizontal member,
  (ii) a vertical member slidably guiding vertical movement of said platform,
  (iii) means for slidably lifting said platform and coating metering assembly on a course guided by said vertical member, whereby said coating metering assembly and platform can be moved between a first position in which said applicator roller is locked into position to deliver coating to said blanket cylinder of said lithographic press unit, and a second position horizontally and vertically displaced from said first position a distance allowing substantial access between the last press unit and the work-piece delivery area adjacent said last press unit, when said press unit is operating as an offset lithographic press unit.

2. The apparatus of claim 1 wherein said horizontal member comprises a horizontal guide shaft attached along the outside of the press unit, and said platform is adapted to engage a support cooperatively and slidably engaging said horizontal guide shaft.

3. The apparatus of claim 2 wherein said vertical member comprises a vertical guide shaft attached to said support.

4. The apparatus of claim 3 wherein said vertical guide shaft extends from the support, through an opening in the platform, to a bearing block positioned above and attached to said support, said platform slidably engaging said vertical shaft, whereby vertical movement of said platform is guided by said vertical guide shaft.

5. The apparatus of claim 4 wherein said means for slidably lifting said platform and coating metering assembly comprises a lift shaft connected to said platform, extending through said bearing block and further attached to a force transmitting member.

6. The apparatus of claim 5 wherein said force transmitting member is an extension plate attached to the lift shaft.

7. The apparatus of claim 5 wherein said apparatus further comprises a force-delivering means positioned to deliver force to said force receiving member.

8. The apparatus of claim 1 wherein said means for slidably lifting the platform and coating metering assembly comprises a cylinder driven by pressurized fluid.

9. The apparatus of claim 8 comprising a pair of said cylinders, each member of said pair being positioned on opposite sides of said platform, and
fluid pressure supply means connected through a pressure-compensated flow divider to each member of said pair, said flow divider being adapted to maintain equal flow to each member of said pair.

10. The apparatus of claim 5 comprising: (a) at least two horizontal guide shaft, one of said horizontal guide shafts being on each side of the press unit; (b) at least two vertical guide shafts, one of said vertical guide shafts being on each side of said platform, and (c) at least two lift shafts, one of said lift shafts being connected to each side of said platform.

11. The apparatus of claim 3 further comprising a bracket attached to the press work-piece delivery in position to support said platform in said second position.

12. The apparatus of claim 11 comprising a lock positioned to removably lock said platform in said first position.

13. The apparatus of claim 12 wherein said lock comprises threaded attachment means for locking said platform in said first position.

14. Apparatus for applying a liquid coating to the surface of a sheet workpiece, said apparatus being adapted for operation on-line with the last unit of an offset lithographic sheet printing press, said press unit comprising a blanket cylinder and a work-piece delivery area, positioned on the opposite end of a well from said blanket cylinder, said apparatus comprising:
(a) a coating metering assembly supported by a platform comprising,
(i) a rotably mounted applicator roller,
(ii) coating supply means for supplying coating to said applicator roller, and
(iii) metering means to control the amount of coating on said applicator roller; and
(b) a guide assembly adapted to retract said platform and said coating metering assembly away from said lithographic press unit, said guide assembly comprising,
(i) a horizontal member and means for slidably supporting said platform movement along said horizontal member,
(ii) a vertical member slidably guiding vertical movement of said platform,
(iii) means for slidably lifting said platform and coating metering assembly on a course guided by said vertical member,
whereby said coating metering assembly and platform can be moved between a first position in which said platform is locked into position to deliver coating to said blanket cylinder of said lithographic press unit, sand a second position horizontally and vertically displaced from said first position a distance allowing substantial access between said last press unit and the work-piece delivery area adjacent said last press unit, when said press unit is operating as an offset lithographic press unit.

* * * * *

UNITED STATES PATENT AND TRADEMARK OFFICE
CERTIFICATE OF CORRECTION

PATENT NO. : 4,825,804
DATED : May 2, 1989
INVENTOR(S) : Mark A. DiRico et al.

It is certified that error appears in the above-identified patent and that said Letters Patent is hereby corrected as shown below:

Change the inventor's name from "Mark A. Dirico" to --Mark A. DiRico--.

U.S. Patent Documents, 4,685,414, "Direco" should be --DiRico--.

Column 1, line 32, "(i)a" should be --(i) a--.

Column 2, line 15, "DRAWINGS" should be on separate line as a subheading.

Column 2, line 58, delete "by" (first occurrence).

Column 5, line 35, "shaft" should be --shafts--.

Signed and Sealed this

Twenty-fourth Day of April, 1990

Attest:

HARRY F. MANBECK, JR.

*Attesting Officer*  *Commissioner of Patents and Trademarks*